United States Patent [19]
Kowalyk

[11] Patent Number: 5,281,141
[45] Date of Patent: Jan. 25, 1994

[54] DENTAL LASER APPARATUS AND METHOD FOR TREATING TOOTH DECAY

[75] Inventor: Kenneth Kowalyk, Hilton Head Island, S.C.

[73] Assignee: Medical Laser Technology, Inc., Hilton Head Island, S.C.

[21] Appl. No.: 851,657

[22] Filed: Mar. 16, 1992

[51] Int. Cl.$^5$ .......................... A61C 5/00; A61B 17/36
[52] U.S. Cl. ...................................... 433/215; 606/10; 606/13; 606/16
[58] Field of Search .......................... 433/215, 216, 29; 606/2, 3, 10, 15, 16

[56] References Cited

U.S. PATENT DOCUMENTS

| | | | |
|---|---|---|---|
| 3,769,963 | 11/1973 | Goldman et al. | |
| 4,347,233 | 6/1982 | Yamauchi et al. | 424/7 |
| 4,461,294 | 7/1984 | Baron | |
| 4,521,194 | 6/1985 | Myers et al. | 433/215 |
| 4,736,745 | 4/1988 | Gluckman | |
| 4,818,230 | 4/1989 | Myers et al. | 433/215 |
| 4,836,782 | 6/1989 | Gonser | 433/229 |
| 4,840,174 | 6/1989 | Gluckman | |
| 4,874,315 | 10/1989 | Featherstone et al. | 433/215 |
| 4,940,411 | 7/1990 | Vassiliadis et al. | 433/215 |
| 4,951,663 | 8/1990 | L'Esperance, Jr. | 128/395 |
| 5,002,051 | 3/1991 | Dew et al. | 128/395 |
| 5,020,995 | 6/1991 | Levy | 433/215 |
| 5,055,048 | 10/1991 | Vassiliadis et al. | 433/215 |
| 5,059,191 | 10/1991 | Beyer et al. | 606/2 |
| 5,071,416 | 12/1991 | Heller et al. | 606/3 |
| 5,071,422 | 12/1991 | Watson et al. | 606/128 |
| 5,092,864 | 3/1992 | Hayes et al. | 606/10 |

FOREIGN PATENT DOCUMENTS 2597745 10/1987 France ................. 433/215
9011728 10/1990 PCT Int'l Appl. ............. 433/216

OTHER PUBLICATIONS

Article, "In vitro caries removal", Terry D. Myers, et al., *CDS Journal*, May 1988.
Article, "The use of a laser for debridement of incipient caries", Terry D. Myers, et al., *The Journal of Prosthetic Denistry*, vol. 53, No. 6, Jun. 1985.
Article, "The soft laser: Therapeutic tool or popular placebo?", Petra Wilder-Smith, Dr., *Oral Surgery*, vol. 66, No. 6, Dec. 1988.
Article, "Scanning Electron Microscopic Study of Laser-Induced Morphologic Changes of a Coated Enamel Surface", John A. Hess, Lasers in Surgery and Medicine, 10:458-462, 1990.
Article, "The use of a caries detector dye in cavity preparation", E. A. M. Kidd, et al. *British Dental Journal*, 1989.
Article, "Clinical guide for removing caries using a caries-detecting solution", Takao Fusayama, *Quintessence International*, vol. 19, No. 6, 1988.

*Primary Examiner*—Gene Mancene
*Assistant Examiner*—Nicholas D. Lucchesi
*Attorney, Agent, or Firm*—Baker & Botts

[57] ABSTRACT

A dental laser apparatus and method is disclosed for removing tooth decay. A substance which selectively attaches to tooth decay is applied to the tooth. This substance has a predetermined absorption band. A laser having an output wavelength which corresponds to the absorption band is supplied and is absorbed primarily by the decayed portions of the tooth. The use of Acid Red 52 dye as the substance and a frequency doubled Nd:YAG laser as the source is disclosed as one embodiment.

17 Claims, 1 Drawing Sheet

DENTAL LASER APPARATUS AND METHOD FOR TREATING TOOTH DECAY

BACKGROUND OF THE INVENTION

1. Field of the Invention

The invention relates generally to a dental laser assembly and method for treating tooth decay. More specifically, it relates to an apparatus and method for selectively removing carious lesions and/or dental decay from human teeth without affecting the adjacent healthy dentin and enamel.

2. Discussion of Prior Art

An all too familiar problem with human teeth is tooth decay. It is well known that a common method of treating tooth decay involves anesthetizing the local area, using a mechanical drill (or similar equipment) to remove the decayed portion of the tooth, placing a restorative material in the cavity area and curing the restorative material. This traditional treatment method has many well known disadvantages. In order to overcome some of these drawbacks, it has been proposed to use a laser to assist in some of the steps of the traditional treatment method.

Over the last 25 years there have been numerous papers, patents, and studies relating to the use of various types of lasers as a medical tool. In particular, $CO_2$, Argon and Nd:YAG lasers have been proposed for a variety of applications and have been used for a number of "soft tissue" dental procedures, for example, cutting tissue. However, "hard tissue" dental applications for the laser have been slower in coming due to a number of complex issues. "Hard tissue" dental applications include, for example, using a laser to remove enamel and/or tooth decay.

One problem heretofore encountered with "hard tissue" dental applications is the management and dissipation of excess laser generated thermal energy before such energy damages the healthy dentin, enamel, pulp, and/or tissues which are in close proximity to the decayed or carious areas to be treated. Previous studies have suggested that the use of the laser to remove tooth decay is severely limited since the power level necessary for the laser to effectively ablate or eradicate the decay produces significant amounts of heat which can kill the tooth nerve and cause other undesirable affects.

Nevertheless, a number of techniques and methods have been suggested which claim to overcome some of the drawbacks described above. For example, U.S. Pat. No. 5,055,048 issued to Vassiliadis et al. discloses an Nd:YAG laser dental assembly for use in eradicating carious lesions in teeth and for a variety of other applications. In Vassiliadis et al., the laser is excited so that the laser emits a laser beam along a predetermined axis that is in line with a fiber optic delivery system and at a pulse rate of 1 to 10,000 pulses per second and with an average power variable from 1/10th to 50 watts. A handpiece is dimensioned to be inserted into a human mouth while an optical fiber optically connects the laser output to the handpiece. The laser assembly also includes a continuous output aiming laser which, upon activation, provides a continuous laser aiming beam coaxial with the treatment beam. Both beams are introduced into the fiber optic delivery system.

In the BACKGROUND OF THE INVENTION section of the Vassiliadis et al. patent, the inventors discuss the use of Nd:YAG laser systems for medical surgical applications. It is disclosed that these previously known laser systems typically have been constructed to provide very high average powers, i.e., in the range of 60 to 100 watts of continuous power. However, various drawbacks of this type of system are asserted. It is further asserted that there has never been an Nd:YAG laser system particularly suited for dental laser applications such as eradication of carious lesions and other applications.

As disclosed in U.S. Pat. No. 5,002,051 issued to Dew et al., optical energy generated by lasers has been applied in recent times to various medical and surgical procedures because the monochromatic and coherent nature of the light generated by lasers has been shown to have absorbency characteristics which vary with the nature of the illuminated tissue. Thus, for a given tissue type, the laser light may propagate through the tissue, substantially unattenuated, or may be almost entirely absorbed. The extent to which the tissue is heated, and ultimately destroyed, depends on the extent to which it absorbs the optical energy. According to Dew et al., it is generally preferred that the laser light be essentially transmissive in tissues which are desired not to be affected, and absorbed by the tissues which are to be affected.

It is further stated in Dew et al. that a known advantage of a laser system is that the optical energy can be delivered to the tissues desired to be operated upon in a precise location and at predeterminable energy levels. The precision with which the laser energy can be directed is enhanced by its ability to be guided by known thin optical fibers. Various types of lasers are discussed. For example, it is stated that argon lasers emit energy at 0.488 and 0.515 micrometers, carbon dioxide ($CO_2$) gas lasers emit energy at a wavelength of 10.6 micrometers and that Nd:YAG lasers have a predominate mode of operation at a wavelength of 1.06 micrometers.

Other patents also disclose using a laser for various dental applications. For example, U.S. Pat. No. 4,818,230 issued to Myers et al. discloses a method for removing dental decay and carious lesions from human teeth comprising the steps of aiming a pulsed laser so that its output impinges upon the decay and repeatedly activating the laser in a pulsed mode until the decay is eradicated from the tooth. The use of a YAG laser with an energy output of 0.1-100 millijoules is disclosed.

U.S. Pat. No. 4,521,194 issued to Myers et al. also discloses a method of removing carious lesions and/or stain from human teeth comprising the steps of aiming a YAG laser so that its output impinges upon the lesion and/or stain and thereafter repeatedly activating the laser in a pulsed mode until the undesired characteristic is removed. The YAG laser is disclosed as producing an energy output of 1-100 millijoules.

U.S. Pat. No. 5,020,995 issued to Levy discloses the use of a laser for removal of tooth and gum tissue. Levy discloses that the enamel and dentin of a tooth include, as one component, hydroxyapatite, which is in amorphous form in the dentin and crystalline form in the enamel. Levy further discloses that healthy dentin is in mineralized form, while dentin which has experienced decay is in demineralized form. Levy also discloses that it has been found that hydroxyapatite absorbs laser radiation in the wavelength range of 9-11 $\mu m$, such as produced by $CO_2$ lasers, and also in the wavelength range 0.5-1.06 $\mu m$, which includes the wavelength that can be produced by a YAG laser.

Levy further states that laser radiation absorption by the various parts of a tooth at various wavelengths is influenced by the absorption of the radiation energy by the water component thereof and that the greater the absorption by water, the less energy is available for absorption by the other components. Levy also states that is has been found that radiation at a wavelength of 1.06 μm (the output of a Nd:YAG laser) is absorbed to a lesser degree by water, and therefore has a greater effect on mineralized tissues. It is said that laser radiation at a wavelength of 0.532 μm (the output of a frequency doubled Nd:YAG laser) is not absorbed at all by water and can be effective on mineralized tissues if a sufficiently high, and thus dangerous, power level is employed. Levy further states that while a particular wavelength may inherently have a cutting effect on enamel or dentin, it has been found that the practical utilization of radiation at such a wavelength for dental procedures is highly dependent on the form in which the radiation is applied, with respect to the energy level, pulse duration and repetition rate. Specifically, it is stated that efforts to apply such radiation in the form of high energy pulses of short duration have been found to produce a highly localized temperature increase, resulting in differential thermal expansion which can cause mechanical damage to the tooth as well as vascular damage to pulp tissue. Conversely, low energy pulses of long duration are said to cause a more widespread heating of the tooth which results in patient discomfort as well as pulp damage due to heating. These are all undesirable drawbacks.

Levy proposes using a 1.06 μm wavelength in the form of pulses having an energy content of between 10 and 50 millijoules, with a pulse duration on the order of 100–300 microseconds, and a repetition rate on the order of 50 Hz. Levy states that laser radiation at a wavelength of 1.06 μm which can be produced by an Nd:YAG laser, can be used for cutting or vaporizing demineralized, i.e., decayed enamel and dentin, without endangering gum tissue. However, Levy states that laser radiation at a wavelength of 0.532 μm can also be used, but this requires great care because it has been found that radiation at this wavelength will also cut gum tissue. Therefore, radiation at this wavelength, Levy concludes, can be used when it is desired to cut gum tissue. Levy further states that radiation at a wavelength of 0.532 μm has been found to be effective only if applied at dangerously high energy levels. These statements in Levy highlight some of the previously believed disadvantages of using a 0.532 μm wavelength, which corresponds to the frequency doubled output of an Nd:YAG laser.

Levy further discloses that 1.06 μm can be used to cut healthier, mineralized dentin and healthy enamel if a dark colored region is first provided at the spot where cutting is to begin. Levy further discloses that when the radiation is applied to demineralized enamel or pathological dentin, a dark spot is not necessary.

In effect, Levy appears to suggest merely coating the surface of a tooth with a dark substance. Presumably, Levy is suggesting something similar to what is disclosed in the article entitled "Scanning Electron Microscopic Study of Laser-Induced Orphologic Changes of a Coated Enamel Surface", Hess, John, *Lasers in Surgery and Medicine*, 10:458–462 (1990), where it is disclosed that the use of a waterproof India ink is suitable for use as a laser initiator with a 1.06 μm wavelength output of an Nd:YAG laser. However, this substance is used to merely coat the tooth and does not selectively attach itself to decayed areas.

While it is clear that several attempts have been made to enable a laser to be used to eradicate tooth decay, various drawbacks still exist. In order to overcome some of the drawbacks, the present invention proposes the use of a selected laser in combination with a substance which selectively attaches itself to tooth decay to concentrate the laser energy on the decayed portions of the tooth. While at least one substance which attaches itself to tooth decay is known, such a substance has been proposed for use merely to visibly detect caries. For example, Acid Red 52 in a solvent, e.g. propylene glycol, has been used to visibly detect the existence of caries. Acid Red 52 in propylene glycol is believed to be advantageous for this purpose because the outer carious dentin is stainable by the solution because the outer carious dentin has collagen fibers which are loosened by the irreversible breakdown of the intermolecular crosslinks, whereas the inner carious dentin and normal dentin, which are unstainable, have solid collagen fibers with undisturbed molecular structure. This is disclosed, e.g. in an article entitled "Clinical Guide For Removing Caries Using a Caries Detecting Solution", Fusayama, T., *Quintessence International*, Vol. 19, No. 6/1988, p. 397–401.

However, this article appears to simply propose the use of this solution to enable visualization of caries while reducing enamel with a high-speed air turbine. With such a turbine device, however, it is said to be necessary to use water to prevent pain caused by friction heat. It is further disclosed that the carious dentin must be reduced at low speed with a round steel bit since the use of a high-speed turbine is apt to induce pain. These are all obviously undesirable drawbacks. Moreover, it suggests that Fusayama fails to recognize that Acid Red 52 can be used in combination with an appropriately selected laser to remove tooth decay.

SUMMARY OF THE INVENTION

It is an object of the present invention to overcome these and other drawbacks of the prior art.

It is an object of the present invention to provide a practical and satisfactory dental laser apparatus.

It is an object of the present invention to provide a practical and satisfactory dental laser method.

It is a further object of the invention to provide an apparatus which improves upon the existing prior art and is especially efficient, effective, and extremely safe.

It is a further object of the invention to provide a method which improves upon the existing prior art and is especially efficient, effective, and extremely safe.

It is a further object of the invention to remove tooth decay by using a substance which selectively attaches itself to the tooth decay and which has certain absorptive characteristics and a laser which is chosen to have corresponding characteristics.

In order to accomplish these and other objects, according to one embodiment of the present invention, there is provided a laser source capable of producing an output radiation beam having a predetermined wavelength. Preferably, the beam is capable of being transmitted along an optical axis, via suitable optic elements, to a handpiece which may be used to direct the beam to at least a portion of a tooth containing tooth decay. Preferably, the tooth is treated with a substance which selectively attaches itself to the decayed portions of the tooth and does not attach itself to healthy portions of the tooth, and the substance has predetermined absorption properties which correspond to the predetermined wavelength of the beam. In this way, the laser beam which is directed to the tooth by the handpiece is primarily absorbed by the decayed portions of the tooth and does not harm the healthy portions of the tooth.

According to another aspect of the invention, there is provided a novel method of safely and effectively using a laser to remove tooth decay without harming healthy portions of the tooth or other surrounding portions. According to the novel method, the tooth decay is treated with a predetermined substance, for example, a dye solution, which will selectively attach itself to the decay without attaching itself to the adjacent healthy dentin, enamel or surrounding tissues. Preferably, the substance is selected so that it attaches to a breakdown in collagen fibers, which is a characteristic of tooth decay. The substance preferably has particular absorptive properties and imparts these absorptive properties only to the decayed portion of the tooth to which it is attached. Then, a laser output having an output wavelength which corresponds to the absorptive characteristics of the substance is applied to the decayed portion of the tooth. Due to the selective absorption of the laser by the substance attached to the decayed portion of the tooth, the decayed area absorbs the laser energy and is removed. The treated decay can be easily flaked off or removed with an appropriate instrument such as a spoon excavator. This process can then be repeated until all of the decay is removed. According to a novel aspect of the present invention, it has been determined that the applying of a dye (e.g., Acid Rhodamine B, also known as Acid Red 52) in solution with propylene glycol to a tooth having decay and subjecting the tooth to the output of a frequency doubled Nd:YAG laser having an output wavelength of 532 nm is particularly advantageous and very effective for removing tooth decay.

DETAILED DESCRIPTION OF THE PREFERRED EMBODIMENTS

Figure 1:
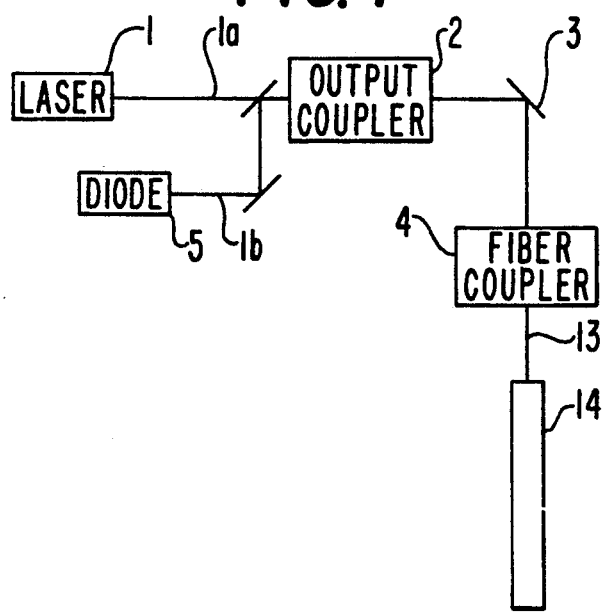
FIG. 1 depicts an apparatus for carrying out one embodiment of the present invention.

With reference to FIG. 1, there is disclosed a laser source 1 which is capable of producing a laser beam $1a$, an output coupler 2 and a mirror 3 which reflects the beam to a fiber coupler 4. Optionally, the laser beam $1a$ may be joined by an aiming beam $1b$, which may be produced by diode 5, and which may travel coaxially with the laser beam, in a known manner, along a fiber optic cable 13 to a commercially available laser handpiece 14.

According to the present invention, for the selective removal of dental decay, without damage to the healthy surrounding portions of the tooth, the area to be treated is initially prepared by application of a substance which will selectively adhere to the carious lesion or decay without adhering to the healthy adjacent dentin, enamel, and tissues. For example, the substance may be a substrate selective non-carcinogenic dye solution, such as Acid Rhodamine B ($C_{27} H_{29} O_7 N_2 S_2 N$) also known as Acid Red 52, also known as Food Red 106, in propylene glycol. This solution has been found to be particularly appropriate because of its adherence to the breakdown of collagen fibers which are a characteristic of tooth decay. The dye solution may be, for example, a 1 percent Acid Red 52 solution in propylene glycol. The solution may be applied to the tooth with an $\frac{1}{8}''$ class 100 foam tip dye applicator. The dye selectively attaches itself to the carious lesion imparting its absorptive properties to the decayed tissue only. After a brief amount of time to enable the dye to travel through and attach to the decay (e.g. 10 seconds) the dye which has not attached may be rinsed away, if desired.

Figure 3:
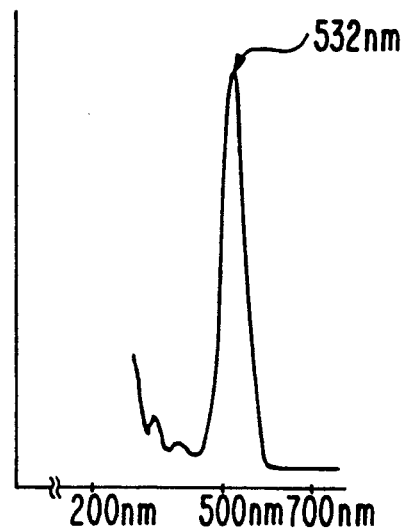
FIG. 3 depicts the absorption band for Acid Red 52.

Other substances may also be used. However, the substance should preferably have an absorption band that includes a wavelength that corresponds to a wavelength which can be produced by a laser. For example, the absorption band for Acid Red 52 is shown in FIG. 3. The frequency doubled Nd:YAG output of 532 nm falls within the absorption band of the Acid Red 52 and substantially corresponds to the absorption peak thereof as shown in FIG. 3. Therefore, for removal of tooth decay this dye/laser combination is believed to be particularly effective and is believed to be heretofore unknown. However, other substances and lasers may be used. For example, any substance which selectively attaches itself to decay may be used in combination with a laser selected to have a wavelength which corresponds to an absorption characteristic of the substance. Preferably, the absorption characteristic is the absorption peak of the substance.

Figure 2:
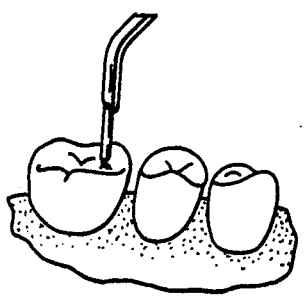
FIG. 2 depicts a block diagram of the application of a laser output to a tooth in accordance with one embodiment of the present invention.

In operation, the 532 nm laser output is delivered to the dyed caries via the conventional fiber optic delivery system as shown in FIG. 2. The laser energy is administered to the tooth by bringing the end of the fiber optic into the proximity of the tooth, for example, by contacting the tip of the fiber optic to the dyed area of tooth decay. This method gives the practitioner a good tactile sense during the delivery of the laser energy to the carious lesion. Fifteen second intervals of 380 Mw, 50 $H_z$, and 200 $\mu s$ pulse width are preferable, but the invention is not so limited.

Preferably, the frequency doubled Nd:YAG has a pulse repetition rate of between one and 10,000 pulses/sec., an average power up to 100 watts, a pulse duration of between a pico second and several milliseconds, and a peak energy of up to five joules/pulse.

Treated decay can then be easily flaked off with a spoon excavator and the dye treatments may be repeated until all of the decay is removed. No conventional anesthesia is required.

The cavity may then be filled in a known manner with a commercially available restorative material.

The foregoing is a description of the preferred embodiments of the present invention. However, the invention is not so limited. Numerous variations and modifications will be apparent to one of ordinary skill in the art within the scope of the invention. The invention is only limited by the claims appended hereto.

I claim:

1. A method of treating a tooth having tooth decay, said method comprising the steps of:
   a. applying a predetermined substance to at least a portion of said tooth, said substance having a selected wavelength absorption property;
   b. subjecting said substance to a laser output having a wavelength selected to correspond to said wavelength absorption property of said substance to destroy at least a portion of said tooth decay; and c. repeating steps a-b until substantially all of the tooth decay is removed; wherein said step f applying a predetermined substance comprises applying to said tooth Acid Red 52.

2. The method of claim 1 wherein said step of subjecting said substance to a laser output comprises subjecting said substance to a frequency doubled Nd:YAG laser output.

3. The method of claim 1 wherein said step of subjecting said substance to a laser output comprises subjecting said substance to approximately a 532 nm laser output.

4. A method of treating a tooth having tooth decay, said method comprising the steps of:
a. applying a predetermined substance to at least a potion of said tooth, said substance having a selected wavelength absorption property;
b. subjecting said substance to a laser output having a wavelength selected to correspond to said wavelength absorption property of said substance to destroy at least a portion of said tooth decay; and
c. repeating steps a-b until substantially all of the tooth decay is removed; wherein said step of applying a predetermined substance comprises applying to said tooth Acid Red 52 in solution with propylene glycol.

5. The method of claim 4 wherein said step of subjecting said substance to a laser output comprises subjecting said substance to a frequency doubled Nd:YAG laser output.

6. The method of claim 4 wherein said step of subjecting said substance to a laser output comprises subjecting said substance to approximately a 532 nm laser output.

7. A method of treating a tooth having tooth decay, said method comprising the steps of:
a. applying a predetermined substance to at least a portion of said tooth, said substance having a selected wavelength absorption property;
b. subjecting said substance to a laser output having a wavelength selected to correspond to said wavelength absorption property of said substance to destroy at least a portion of said tooth decay; and
c. repeating steps a-b until substantially all of the tooth decay is removed; wherein said step of applying a predetermined substance comprises applying to said tooth a substance which selectively attaches to a breakdown of collagen fibers.

8. The method of claim 7 wherein said step of subjecting said substance to a laser output comprises subjecting said substance to a frequency doubled Nd:YAG laser output.

9. The method of claim 7 wherein said step of subjecting said substance to a laser output comprises subjecting said substance to approximately a 532 nm laser output.

10. The method of claim 7 wherein said laser output wavelength is approximately 532 nm and said substance has an absorption band including 532 nm.

11. The apparatus of claim 10 wherein said substance has an absorption peak of approximately 532 nm.

12. The method of claim 7 wherein said laser output is a frequency doubled Nd:YAG output and said substance has a absorption band including 532 nm.

13. The apparatus of claim 1 wherein said substance has an absorption peak of approximately 532 nm.

14. The method of claim 7 wherein said substance is Acid Red 52 and said laser output wavelength is approximately 532 nm.

15. The method of claim 7 wherein said substance is Acid Red 52 and said laser output is the output of a frequency doubled Nd:YAG laser.

16. The method of claim 7 wherein said substance has at least one absorption peak at a predetermined wavelength and said laser output comprises a wavelength corresponding to said predetermined wavelength.

17. A method of treating a tooth having tooth decay, said method comprising the steps of:
a. applying a predetermined substance to at least a portion of said tooth, said substance having a selected wavelength absorption property;
b. subjecting said substance to a laser output having a wavelength selected to correspond to said wavelength absorption property of said substance to destroy at least a portion of said tooth decay; and
c. repeating steps a-b until substantially all of the tooth decay is removed; wherein said step of applying a substance comprises applying Acid Red 52 which selectively attaches to tooth decay and which has a wavelength absorption band which includes 532 nm, and said step of subjecting said substance to a laser output comprises subjecting said Acid Red 52 to a laser output having a wavelength of approximately 532 nm.

* * * * *

UNITED STATES PATENT AND TRADEMARK OFFICE
CERTIFICATE OF CORRECTION

PATENT NO. : 5,281,141
DATED : January 25, 1994
INVENTOR(S) : Kenneth KOWALYK

It is certified that error appears in the above-indentified patent and that said Letters Patent is hereby corrected as shown below:

Column 6, line 39, delete "Mw" and insert --mW--; and

Column 7, line 2, after "step" delete "f" and replace with --of--.

Signed and Sealed this

Twenty-third Day of August, 1994

Attest:

BRUCE LEHMAN

Attesting Officer        Commissioner of Patents and Trademarks